United States Patent
Lee et al.

(10) Patent No.: US 11,160,589 B1
(45) Date of Patent: Nov. 2, 2021

(54) SYSTEM AND METHOD FOR JOINING BONEY STRUCTURES

(71) Applicant: Randall F. Lee, Southlake, TX (US)

(72) Inventors: Randall F. Lee, Southlake, TX (US); Daniel S. Savage, Brecksville, OH (US); Alan W. Rorke, Bristol Avon (GB)

(73) Assignee: Randall F. Lee, Southlake, TX (US)

( * ) Notice: Subject to any disclaimer, the term of this patent is extended or adjusted under 35 U.S.C. 154(b) by 0 days.

(21) Appl. No.: 17/175,649

(22) Filed: Feb. 13, 2021

Related U.S. Application Data

(60) Provisional application No. 63/130,323, filed on Dec. 23, 2020, provisional application No. 63/113,886, filed on Nov. 15, 2020, provisional application No. 63/081,187, filed on Sep. 21, 2020.

(51) Int. Cl.
*A61B 17/80* (2006.01)
*A61B 17/84* (2006.01)

(52) U.S. Cl.
CPC ........ *A61B 17/8004* (2013.01); *A61B 17/844* (2013.01); *A61B 17/846* (2013.01)

(58) Field of Classification Search
CPC .............. A61B 17/846; A61B 17/8014; A61B 17/8004; A61B 17/8052; A61B 17/844; A61B 17/862; A61B 17/8605; A61B 17/74; A61B 17/742; A61B 17/746; A61B 2017/8655; A61B 2017/681
See application file for complete search history.

(56) References Cited

U.S. PATENT DOCUMENTS

| | | | |
|---|---|---|---|
| 3,506,982 | A | 4/1970 | Steffee |
| 3,552,389 | A | 1/1971 | Allgower et al. |
| 4,484,570 | A | 11/1984 | Sutter et al. |
| 4,790,303 | A | 12/1988 | Steffee |
| 6,984,234 | B2 | 1/2006 | Bray |
| 7,572,280 | B2 | 8/2009 | Dickinson et al. |
| 8,267,997 | B2 | 9/2012 | Colleran |
| 8,268,000 | B2 | 9/2012 | Waugh et al. |
| 8,328,872 | B2 | 12/2012 | Duffield et al. |
| 8,361,155 | B2 | 1/2013 | Lambrecht et al. |
| 8,540,769 | B2 | 9/2013 | Janowski et al. |
| 8,641,766 | B2 | 2/2014 | Donner et al. |
| 8,764,831 | B2 | 7/2014 | Lechmann et al. |

(Continued)

FOREIGN PATENT DOCUMENTS

| | | |
|---|---|---|
| AU | 2013224006 B2 | 2/2017 |
| CA | 2635537 C | 5/2014 |

(Continued)

OTHER PUBLICATIONS

Lee et al.; U.S. Appl. No. 17/248,943, filed Feb. 13, 2021.
Notice of Allowance; dated Apr. 28, 2021; by the USPTO; re U.S. Appl. No. 17/248,943.

*Primary Examiner* — Amy R Sipp
(74) *Attorney, Agent, or Firm* — Bill R. Naifeh

(57) ABSTRACT

Disclosed are system and methods that use at least one non-threaded anchor and an implant with at least one aperture to join boney structures, where the interaction of the head of the anchor with the implant aperture causes the anchor to move transversely with respect to an initial trajectory. This movement causes compression or distraction of the boney structures which are coupled to the anchors.

8 Claims, 9 Drawing Sheets

(56) References Cited

U.S. PATENT DOCUMENTS

| | | |
|---|---|---|
| 8,882,775 B2 | 11/2014 | LaPosta et al. |
| 8,968,405 B2 | 3/2015 | Kirwan et al. |
| 8,979,930 B2 | 3/2015 | Glazer |
| 9,351,847 B2 | 5/2016 | Reed et al. |
| 9,408,715 B2 | 8/2016 | Donner et al. |
| 9,526,620 B2 | 12/2016 | Slivka et al. |
| 9,566,165 B2 | 2/2017 | Lee et al. |
| 9,937,055 B1 | 4/2018 | Bernhardt, Jr. et al. |
| 10,022,161 B2 | 7/2018 | Blain |
| 10,098,755 B2 | 10/2018 | Kaufmann et al. |
| 10,195,051 B2 | 2/2019 | Bergey |
| 10,245,156 B2 | 4/2019 | Chataigner et al. |
| 10,258,479 B2 | 4/2019 | Stewart et al. |
| 10,376,377 B2 | 8/2019 | Seifert et al. |
| 10,433,975 B2 | 10/2019 | Ashleigh et al. |
| 10,478,310 B2 | 11/2019 | Ameil et al. |
| 10,485,591 B2 | 11/2019 | Lequette et al. |
| 10,631,999 B2 | 4/2020 | Gilbride et al. |
| 10,758,370 B2 | 9/2020 | Gilbride et al. |
| 2005/0182408 A1* | 8/2005 | Pfefferle ............ A61B 17/8085 606/282 |
| 2006/0195094 A1 | 8/2006 | McGraw et al. |
| 2009/0210062 A1 | 8/2009 | Thalgott et al. |
| 2009/0254126 A1* | 10/2009 | Orbay ............... A61B 17/1728 606/282 |
| 2011/0098747 A1 | 4/2011 | Donner et al. |
| 2012/0078371 A1 | 3/2012 | Gamache et al. |
| 2012/0078373 A1 | 3/2012 | Gamache et al. |
| 2013/0150968 A1 | 6/2013 | Dinville et al. |
| 2013/0166029 A1 | 6/2013 | Dinville et al. |
| 2014/0180417 A1 | 6/2014 | Bergey |
| 2015/0127109 A1 | 5/2015 | Brett |
| 2016/0106550 A1 | 4/2016 | Slivka et al. |
| 2016/0151171 A1 | 6/2016 | Mozeleski et al. |
| 2016/0338853 A1 | 11/2016 | Donner et al. |
| 2017/0007305 A1* | 1/2017 | Hollis ................ A61B 17/1728 |
| 2017/0071750 A1 | 3/2017 | Urban et al. |
| 2017/0246007 A1 | 8/2017 | Chataigner et al. |
| 2018/0177606 A1 | 6/2018 | Reed et al. |
| 2018/0214280 A1 | 8/2018 | Seifert et al. |
| 2018/0325694 A1 | 11/2018 | Petersheim et al. |
| 2019/0000637 A1 | 1/2019 | Gilbride et al. |
| 2019/0183658 A1 | 6/2019 | Lambrecht |
| 2019/0328540 A1 | 10/2019 | Seifert et al. |

FOREIGN PATENT DOCUMENTS

| | | |
|---|---|---|
| CN | 108969163 A | 12/2018 |
| EP | 1968464 B1 | 2/2012 |
| EP | 2419030 B1 | 1/2017 |
| EP | 2701638 B1 | 5/2017 |
| EP | 3207900 B1 | 7/2018 |
| EP | 3470022 A1 | 4/2019 |
| FR | 2954692 A1 | 7/2011 |
| FR | 3005569 A1 | 11/2014 |
| FR | 3016793 A1 | 7/2015 |
| JP | 2017-507000 A | 3/2017 |
| JP | 2018-187417 A | 11/2018 |
| KR | 101555317 B1 | 10/2015 |
| KR | 101636010 B1 | 7/2016 |
| KR | 20160145538 A | 12/2016 |
| RU | 2631208 C2 | 9/2017 |
| WO | 2010/121028 A2 | 10/2010 |
| WO | 2011/129973 A1 | 10/2011 |
| WO | 2013/062716 A1 | 5/2013 |
| WO | 2017/029301 A1 | 2/2017 |
| WO | 2017/186966 A1 | 11/2017 |

* cited by examiner

SYSTEM AND METHOD FOR JOINING BONEY STRUCTURES

CROSS REFERENCE TO RELATED APPLICATIONS

This application claims the benefit of the filing dates of the following U.S. provisional patent applications: U.S. Patent Application Ser. No. 63/081,187, filed on Sep. 21, 2020, entitled SYSTEM AND METHOD FOR JOINING BONEY STRUCTURES; U.S. Patent Application Ser. No. 63/113,886, filed on Nov. 15, 2020, entitled SYSTEM AND METHOD FOR JOINING BONEY STRUCTURES; U.S. Patent Application Ser. No. 63/130,323, filed on Dec. 23, 2020, entitled SYSTEM AND METHOD FOR JOINING BONEY STRUCTURES; the disclosures of all of the above patent applications are hereby incorporated by reference for all purposes. This application also incorporates by reference for all purposes a commonly owned patent application entitled SYSTEM AND METHOD FOR JOINING BONEY STRUCTURES, U.S. patent application Ser. No. 17/248,943, filed on the same date as the present filing.

TECHNICAL FIELD

The disclosed invention relates in general to orthopedic and dental surgically implanted devices, and in particular to implantable devices which use a plurality of non-threaded anchors with an implant or plate to compress and join boney structures.

BACKGROUND INFORMATION

Over a hundred years ago surgeons determined that a combination of screws and plates worked as a method of internal fixation of two or more bone structures. In time surgeons empirically learned that placing two or more bones in mechanical compression greatly improved the speed and quality of bone healing. Mechanical compression was then rendered through external devices and internally fixated with the screw plate device.

Many believe that localized bone compression is the orthopaedic standard for bone healing. Current art uses plates with dedicated screw channels or directive apertures that determine the range of screw angulation and the resultant course of the screw's trajectory.

In many orthopedic related procedures, however, such as spinal, sternal chest closure, dental, and numerous orthopedic reconstructions, plates and screws have not been found to follow compressive bone healing principals. Instead, the screw plate configurations stabilize the boney structures, but do not typically compress the bone structures together. Furthermore, threaded anchors such as screws have many disadvantages, including the tendency to back out of a boney structure over time.

Therefore, what is needed is a novel plate anchor system that consistently achieves bone compression or distraction of two boney structures.

SUMMARY

In response to these and other problems, in one embodiment, there is a system that includes non-threaded anchors that follow a trajectory into a boney structure and then a non-threaded head of the anchor interacts with the aperture features in an implant to cause the head of the anchor to move transversely which can cause compression or distraction of boney structures coupled to the anchors.

These and other features, and advantages, will be more clearly understood from the following detailed description taken in conjunction with the accompanying drawings. It is important to note the drawings are not intended to represent the only aspect of the invention.

DETAILED DESCRIPTION

Figure 1A:
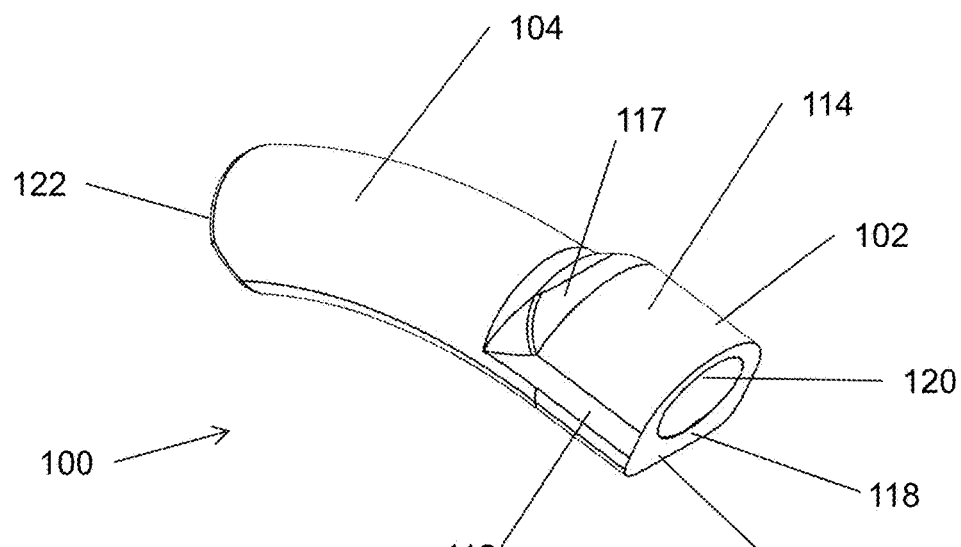
FIG. 1A is a perspective view of one aspect of a non-threaded anchor which can be used in one or more aspects of the present invention.

For the purposes of promoting an understanding of the principles of the present inventions, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the inventions as described herein are contemplated as would normally occur to one skilled in the art to which the invention relates.

When directions, such as upper, lower, top, bottom, clockwise, counter-clockwise, are discussed in this disclosure, such directions are meant to only supply reference directions for the illustrated figures and for orientation of components in respect to each other or to illustrate the figures. The directions should not be read to imply actual directions used in any resulting invention or actual use. Under no circumstances, should such directions be read to limit or impart any meaning into the claims.

Figure 1B:
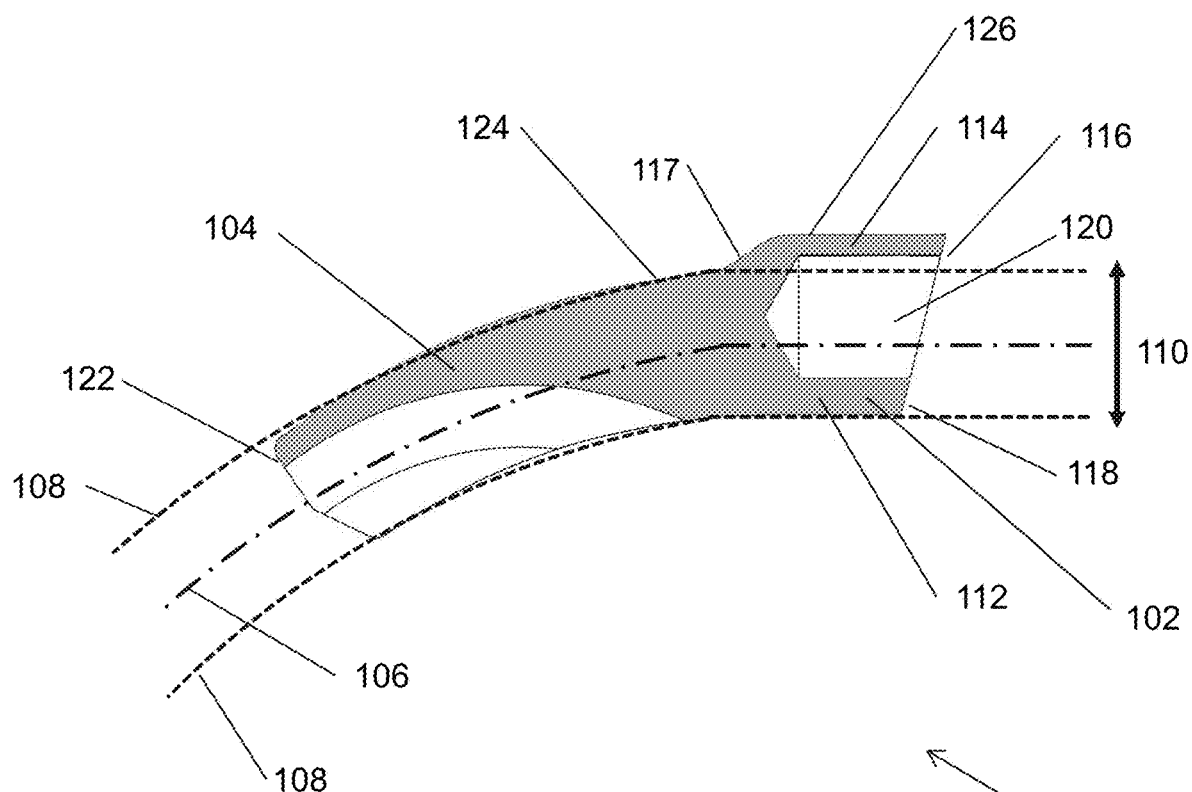
FIG. 1B is a longitudinal section view of the non-threaded anchor of FIG. 1A.
Figure 1C:
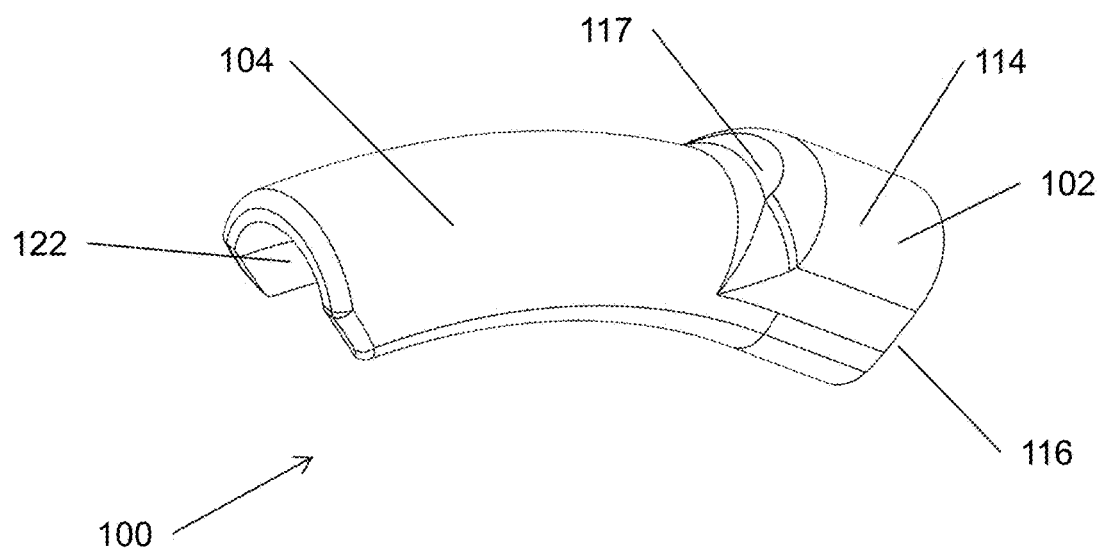
FIG. 1C is a top perspective view of the non-threaded anchor of FIG. 1A orientated so that the distal end is illustrated.
Figure 1D:
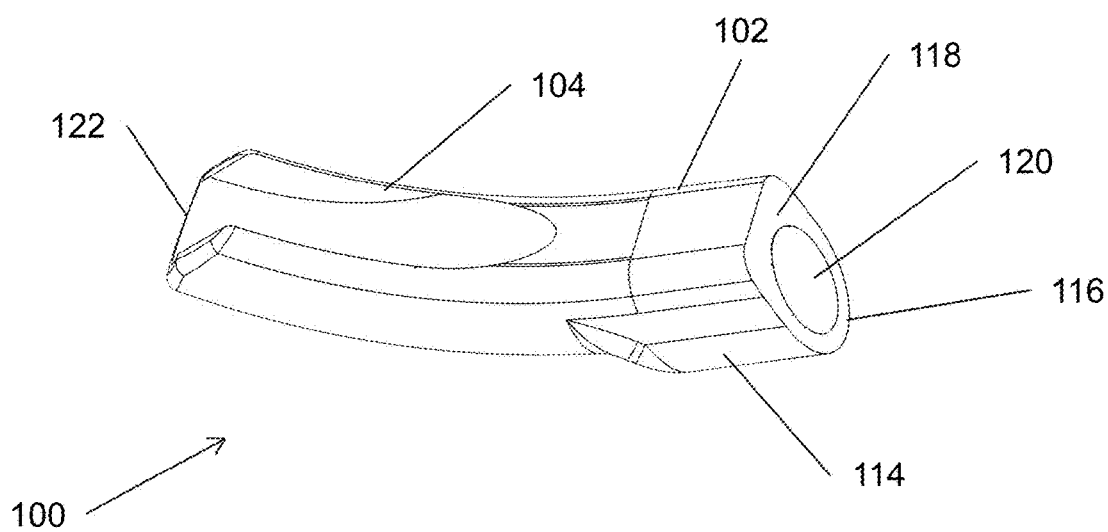
FIG. 1D is a bottom perspective view of the non-threaded anchor of FIG. 1A.

Anchors:

FIG. 1A is a proximal perspective view of one aspect of a non-threaded anchor 100 which can be used with several embodiments of the present invention. FIG. 1B is a longitudinal section view of the non-threaded anchor 100. FIG. 1C is a top perspective view of the anchor 100 orientated to illustrate a distal end 122. In contrast, FIG. 1D is a bottom perspective view of the anchor 100.

Turning now to FIGS. 1A through 1D, in the illustrative embodiment, the non-threaded anchor 100 includes a non-threaded proximal end or head portion 102 which is coupled to a non-threaded elongated body portion 104. The non-threaded elongated body 104 has a longitudinal or center axis 106, which in this embodiment, partially defines an initial trajectory into a boney structure as will further be discussed below. In the illustrated embodiment, the head portion 102 and the elongated body portion 104 share the central axis 106 which is curved within the elongated body portion 104 and straight within the head portion 102. In other embodiments, the elongated body portion 104 may be straight in which the center axis 106 would also be straight. In yet other embodiments, the head portion 102 may be curved and likewise, the center axis 106 within the head portion may also be curved.

FIG. 1B is a section view of the anchor 100 with the addition of dotted lines 108. For purposes of illustration, the dotted lines 108 are boundary lines that represent the portion of the anchor 100 that is generally equal distance with respect to the center axis 106 in a direction 110 that is generally normal or transverse to the direction of the center axis 106. For purposes of this disclosure, any portion of the head portion 102 that is outside of the dotted lines 108 is defined as "offset" or eccentric to the center axis 106. As can be seen most clearly in FIG. 1B, the non-threaded head portion 102 includes a first or symmetrical head portion 112 that is substantially within the boundary lines 108 and a second portion or "offset" portion 114 of the head portion 102 that is outside of the boundary lines 108. Looking from the perspective of FIG. 1B, the boundary lines 108 are generally symmetrical or equal distance from the center axis 106 in a direction 110 which is normal to the center axis. Thus, for purposes of this disclosure, the second or offset portion 114 of the head portion 102 that is outside of the boundary lines 108 is defined as an offset portion 114 from the center axis. In other words, an unsymmetrical mass or structure beyond an equal distance line from the center axis is considered to be an "offset" portion 114 of the head portion 102 for purposes of this disclosure. In this embodiment, a transition or blended surface 117 allows for the smooth transition between the surface of the elongated body portion 104 and the offset anchor head portion 114.

In certain embodiments, a proximal end 116 of the anchor 100 contains an engagement surface 118 that is angled with respect to the normal direction 110 of center axis 106. In certain embodiments, the engagement surface 118 may have engagement features, such as aperture 120 for engaging with various embodiments of insertion instruments. In the illustrative embodiment, the longitudinal axis of the aperture 120 may be parallel with respect to the center axis 106.

Figure 1E:
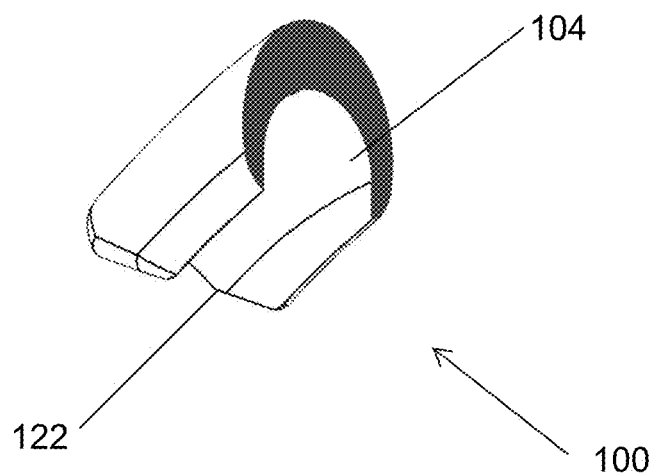
FIGS. 1E through 1H are transverse sectional views of the non-threaded anchor of FIG. 1A.
Figure 1F:
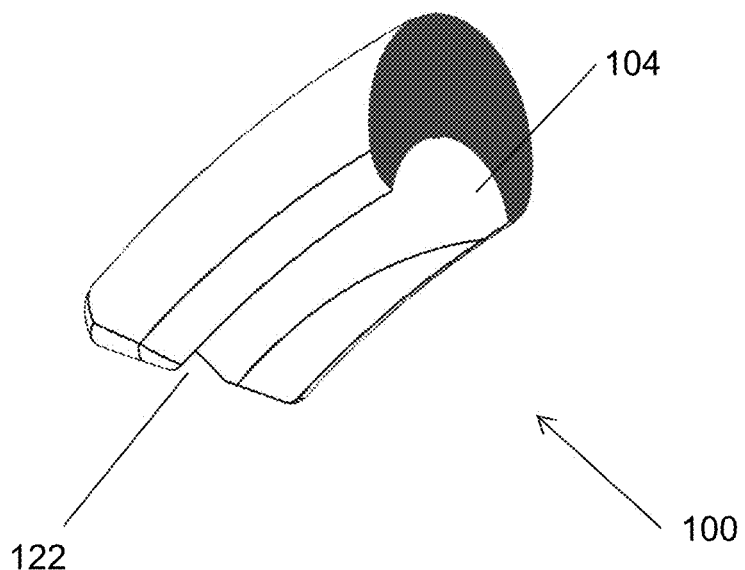

As can be best seen in FIGS. 1C and 1D, a distal end 122 of the anchor 100 is designed to penetrate and be pushed through a boney structure. Consequently, at the distal end 122 the cross-sectional area of the body portion 104 is significantly reduced which also reduces the force necessary to push the distal end 122 through the boney structure (not shown). In the illustrative embodiment as best seen in FIG. 1C, the distal end 122 has a generally semi-circular or horseshoe shaped cross-sectional area. For instance, FIG. 1E is a partial perspective section view where the body portion 104 has been cut close to the distal end 122. The cut in FIG. 1E is in a vertical direction and illustrates the horseshoe shape of cross-section of the body portion 104 when the section is cut close to the distal end 122. In contrast, FIG. 1F is a partial perspective section view where the body portion 104 has been cut at a point between the distal end 122 and a midsection point 124 (see FIG. 1B). The cut in FIG. 1F is in a vertical direction and illustrates a substantial thickening of the horseshoe shape of cross-section of the body portion 104 of the anchor 100.

Figure 1G:
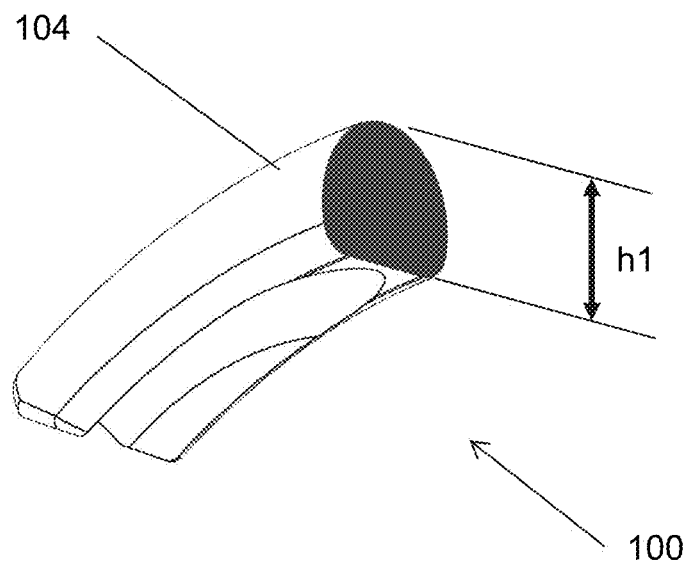
Figure 1H:
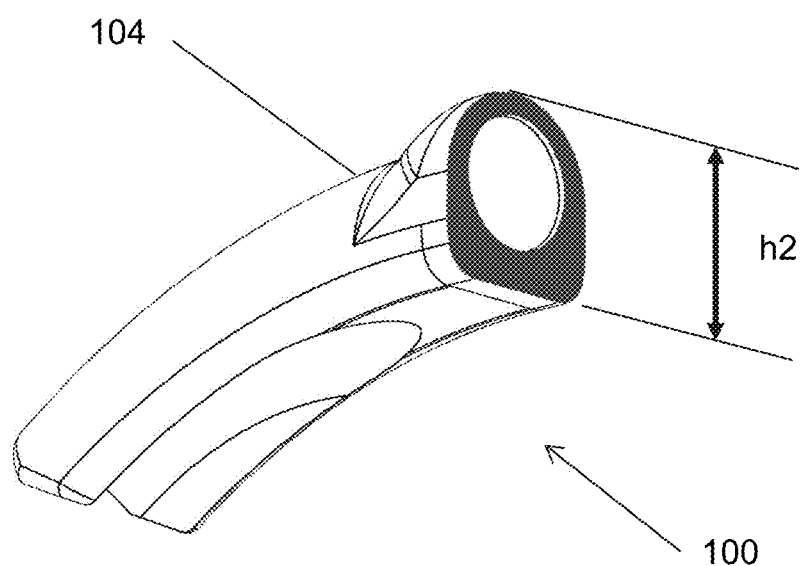

FIG. 1G is a partial perspective view where the body portion 104 has been cut at the midsection point 124 (see FIG. 1B). The cut in FIG. 1G is in a vertical direction and illustrates a cross-sectional shape of a solid partially elliptical segment. As illustrated, the body portion 104 has a vertical thickness or height of h1 at this cut point. In contrast, FIG. 1H is a partial perspective view where the head portion 102 has been cut around a point 126 (see FIG. 1B). As illustrated, the head portion 102 has a vertical thickness or height of h2 at this cut point. Note the difference in between the height h1 in FIG. 1G and the height h2 in FIG. 1H is created by the offset portion 114 of the head portion 102 as discussed above.

Although the anchor 100 as illustrated and discussed above uses a tapering horseshoe cross-sectional shape for the body portion 104, any cross-sectional shape could be used and still be within the inventive aspects of the present invention. Such shapes include triangular, diamond, rectangular, circular or equilateral polygon cross-sectional shapes or a combination thereof. For instance, a triangular cross-sectional shape could be used on the body portion 104 while the head portion 102 may be largely circular in cross-sectional shape. If such shapes are used, generally the body portion will taper down from the head portion 102 to the distal end 122. In other words, the cross sectional areas of the body portion 104 will decrease as the distal end is approached.

In certain embodiments, the anchors discussed above may be fabricated from any number of biocompatible implantable materials, including but not limited to Titanium Alloys (Ti 6Al4V ELI, for example), commercially pure titanium, Chromium Cobalt (Cr—Co) and/or stainless steels. In yet other embodiments, the anchors may also be manufactured from polymer, including Carbon Fiber Reinforced Polymer ("CFRP") with a high carbon mass percentage. Furthermore in some embodiments, as explained below, the anchors may be formed using a shape memory alloy, such as Nitinol®.

Figure 2A:
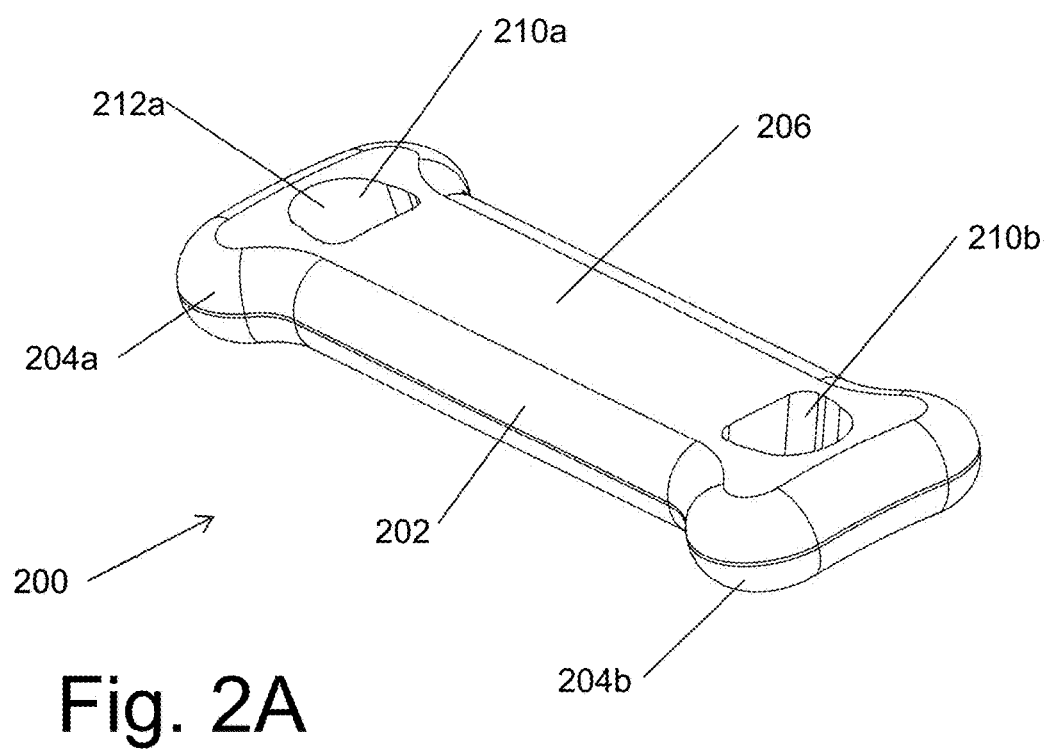
FIG. 2A is an isometric view of one embodiment of an implant which can be used with different aspects of the present invention.
Figure 2B:
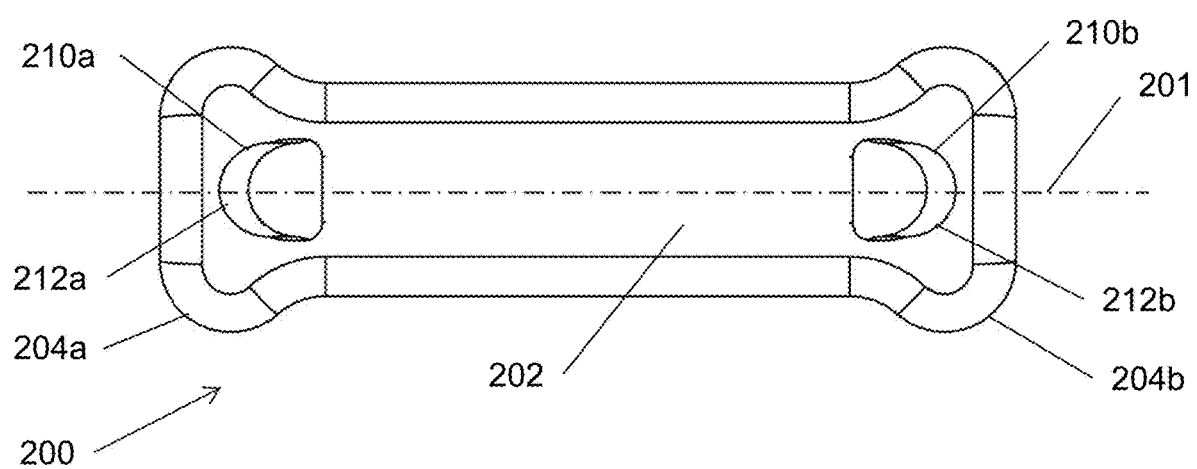
FIG. 2B is an top view of the embodiment of FIG. 2A.
Figure 2C:
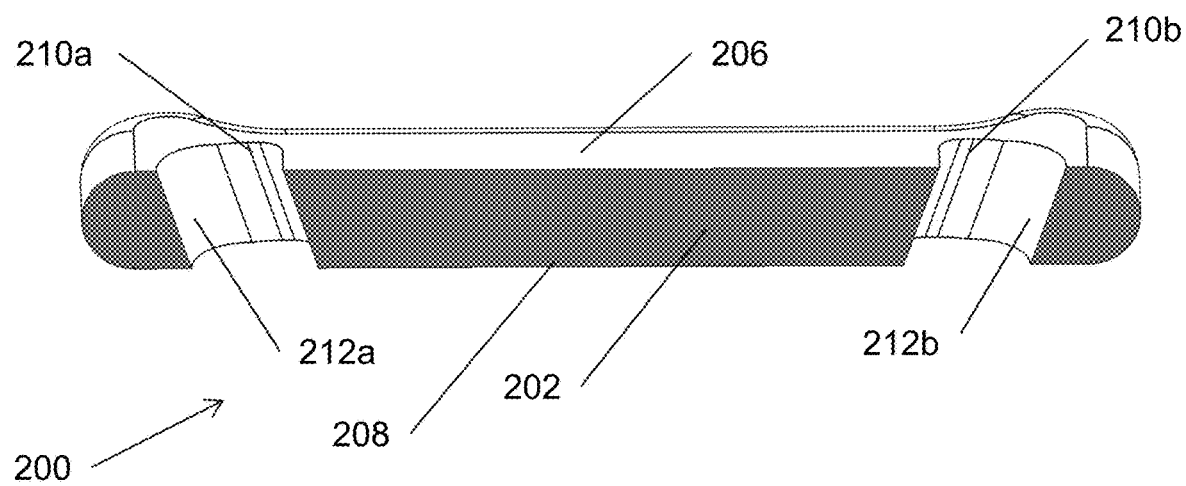
FIG. 2C is a side perspective sectional view of the embodiment of FIG. 2A.

An Embodiment of an Implant:

FIG. 2A is an isometric illustration of a supra bone implant or supra implant (also known in the art as a fixation plate, insert plate, or insert). FIG. 2B is a top view of the supra implant 200 and FIG. 2C is a sectional perspective view of the supra implant 200. The implants disclosed herein, such as supra implant 200, may be manufactured from any number of implant grade materials, including, but not limited to Titanium and Titanium Alloys, as well as Carbon Fiber Reinforced Polymer (CFRP) and shape memory alloys as explained below.

In the illustrated embodiment of FIGS. 2A, 2B and 2C, the supra implant 200 has an elongated main body portion 202 with end portions 204a and 204b on each side of the main body portion. In certain embodiments, the main body portion 202 and the end portions 204a and 204b are all aligned along a longitudinal axis 201 (FIG. 2B). The supra implant 200 has a proximal surface 206 and a distal surface 208 for engaging or for placement next to one or more boney structures.

In certain embodiments, the end portions 204a and 204b have apertures 210a and 210b defined therethrough for accepting a non-threaded anchor, such as anchor 100 described above. In certain embodiments, the apertures 210a and 210b have curved engaging surfaces 212a and 212b defined therein which are sized to receive and engage a surface of the non-threaded anchor 100. In certain embodiments, the interaction of the inwardly sloped engaging surfaces 212a and 212b with the longitudinal shape or geometry of the elongated body portion 104 of non-threaded anchor 100 defines an initial insertion trajectory for the non-threaded anchor. For purposes of this disclosure the "initial trajectory" is the path of movement of the elongated body portion 104 of an anchor 100 starting when the elongated body portion 104 is first introduced into the aperture (e.g. either aperture 210a or 210b of FIG. 3A) and ending when the head portion 102 of the anchor 100 first comes into contact with the engaging surfaces 212a and 212b forming a portion of the inside of the aperture (see FIG. 3C below).

A Method of Use:

FIGS. 3A through 3E demonstrate a method of using at least two anchors 100a and 100b with the supra implant 200 to compress two boney structures 250a and 250b together. For purposes of this disclosure, a boney structure many be an entire human bone or a portion of a bone that has been fragmented or otherwise separated. FIGS. 3A through 3E are cross-sectional views of the implant 200, the boney structures 250a and 250b, and two anchors 100a and 100b showing different stages of interaction between these elements. Anchors 100a and 100b are similar to anchor 100 discussed above with the subscribe reference letters added to distinguish the anchors from one another. For brevity and clarity, a description of those parts which are identical or similar to those described in connection with the implant 200 or the anchor 100 will not be repeated here.

Figure 3A:
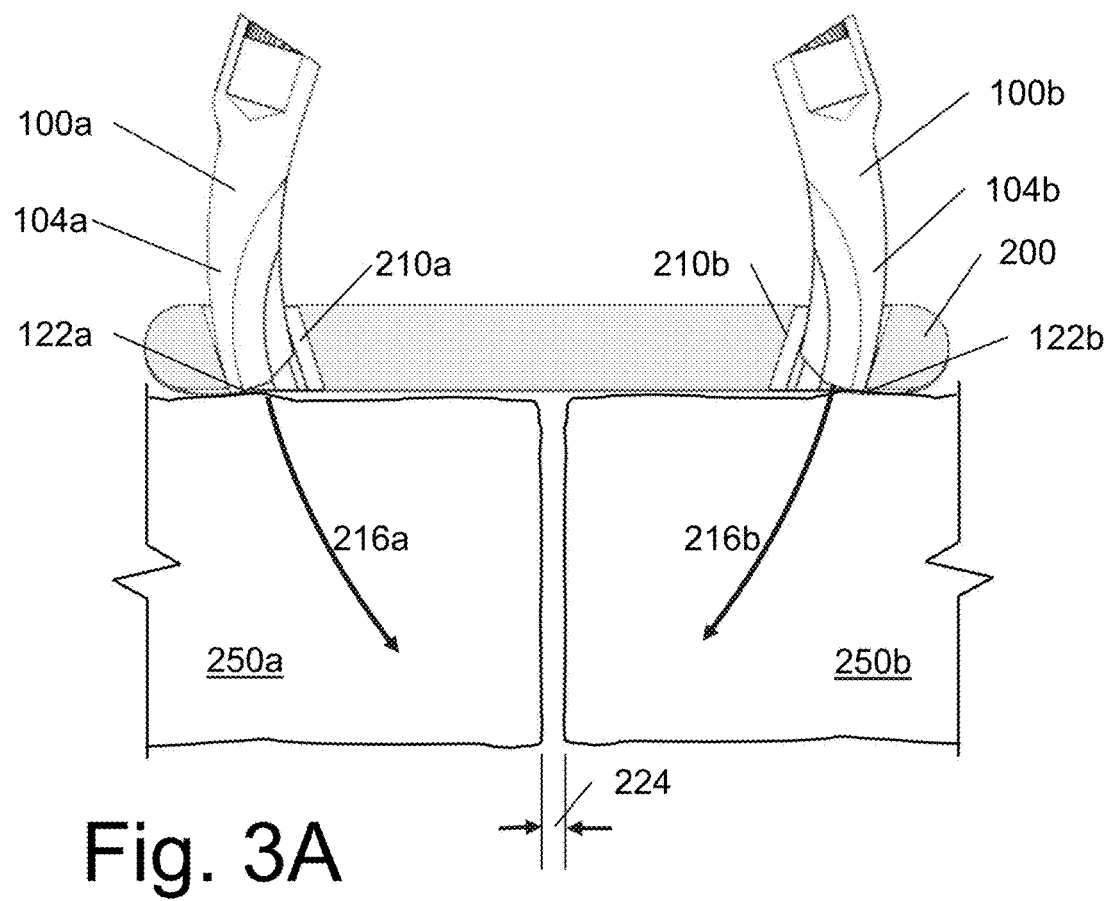
FIGS. 3A through 3E are sectional views illustrating a method of use and the progression of one aspect of anchors proceeding through the implant of FIG. 2A and two boney structures.

In FIG. 3A, the implant 200 is positioned adjacent to the boney structure 250a and the second boney structure 250b. For purposes of explaining the illustrated embodiment, a gap 224 (not drawn to scale) is illustrated between the boney structure 250a and the boney structure 250b. Additionally, for purposes of illustration, an initial trajectory of elongated body portion 104a of anchor 100a can be visualized as arrow 216a. Similarly, an initial trajectory of elongated body portion 104b of anchor 100b can be visualized as arrow 216b. In FIG. 3A, a distal end 122a of the non-threaded elongated body portion 104a is illustrated as having been introduced into the aperture 210a. Similarly, a distal end 122b of the non-threaded elongated body portion 104b is illustrated as having been introduced into the aperture 210b.

Figure 3B:
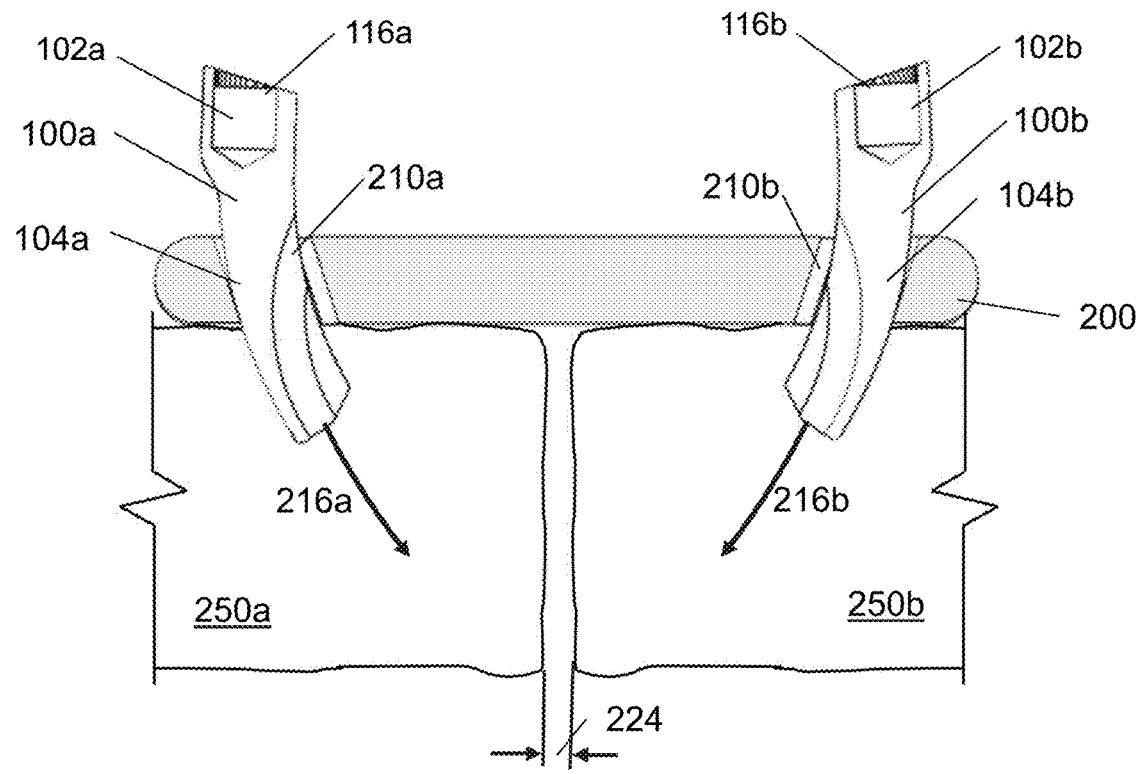

FIG. 3B illustrates the system and boney structures of FIG. 3A, but with the elongated body portions 104a and 104b driven partially into the boney structures 250a and 250b, respectively. In certain embodiments, a smooth non-torsional force may be applied onto the proximal end 116a of the head portion 102a to drive the elongated body portion 104a through the aperture 210a and into the boney structure 250a along the trajectory illustrated as arrow 216a. Additionally, a smooth non-torsional force may be applied onto the proximal end 116b of the head portion 102b to drive the elongated body portion 104b through the aperture 210b and into the boney structure 250b along the trajectory illustrated as arrow 216b. In certain embodiments this non-torsional force may be a "smooth" non-torsional force as opposed to a series of impact forces. In yet other embodiments, an impact force or a rotating force may be applied to drive the elongated body portions 104a and 104b into the boney structures 250a and 250b, respectively.

Figure 3C:
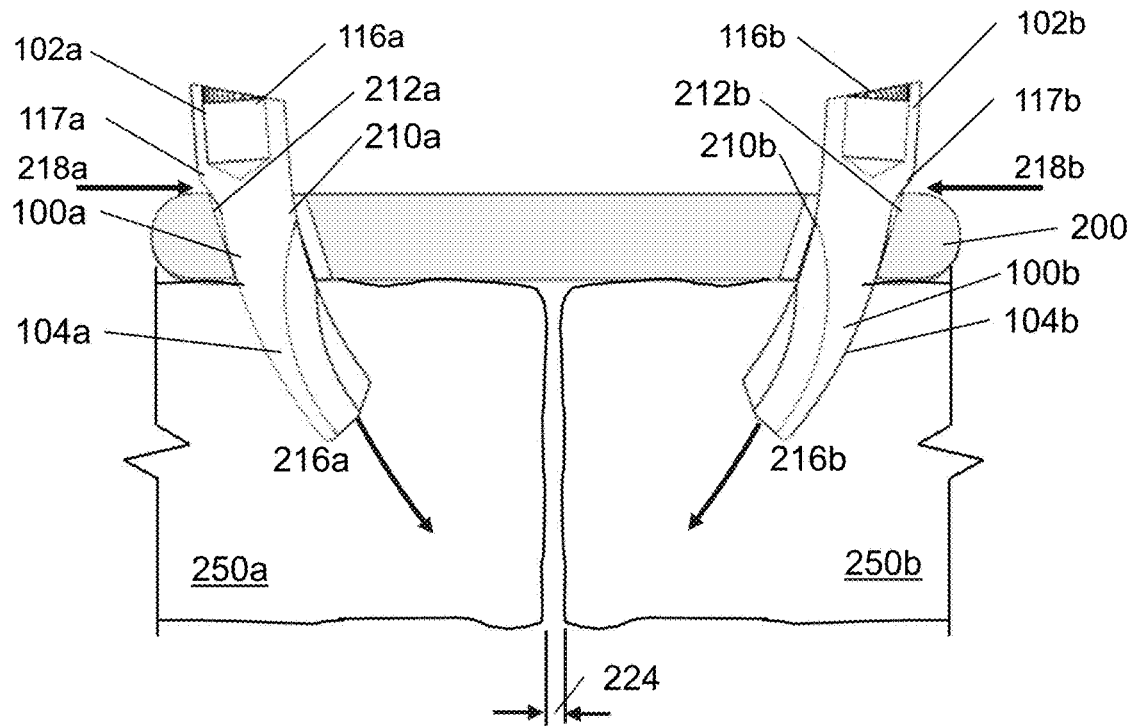

Similarly, FIG. 3C illustrates the system and boney structures of FIG. 3B, but with the elongated body portions 104a and 104b driven farther into the boney structures 250a and 250b, respectively. As can be seen in FIG. 3C, the elongated body portions 104a and 104b have been almost completely driven through the apertures 210a and 210b, respectively and each elongated body portion 104a and 104b are still following their respective initial trajectories as represented by arrows 216a and 216b.

FIG. 3C also illustrates the situation where the non-torsional force continues to be applied onto the proximal end 116a as the transition surface 117a of head portion 102a begins to interact with the engaging surface 212a of the aperture 210a. The interaction between the engaging surface 212a of the aperture 210a and the transition surface 117a of the head portion 102a forces the head to in a direction that is generally transverse to the center axis 106 of the anchor 100a (see FIG. 1B above). The transition surface 117a allows for a smooth transition and kinematic transverse movement. The direction of this transverse movement is represented by the arrow 218a. The transverse movement of the head portion 102a also causes movement of the elongated body portion 104a. Because the boney structure 250a is now attached to the elongated body portion 104a, the boney structure 250a is also forced to move in the transverse direction represented by arrow 218a. Thus, causing the boney structure 250a to move closer to the boney structure 250b.

Simultaneously, a second non-torsional force continues to be applied onto the proximal end 116b as the transition surface 117b of head portion 102b begins to interact with the engaging surface 212b of the aperture 210b. The interaction between the aperture 210b and the transition surface 117b of the head portion 102b forces the head to move in a direction that is generally transverse to the center axis 106 of the anchor 100a (see FIG. 1B above). The direction of this transverse movement is represented by the arrow 218b which is in a direction that is opposite from the direction represented by arrow 218a discussed above. The transverse movement of the head portion 102b also causes movement of the elongated body portion 104b. Because the boney structure 250b is now attached to the elongated body portion 104b, the boney structure 250b is also forced to move in the transverse direction represented by arrow 218b. Thus, causing the boney structure 250b to move closer to the boney structure 250b. Thus, the gap 224 narrows as the head portions 102a and 102b approach their respective apertures 210a and 210b.

Figure 3D:
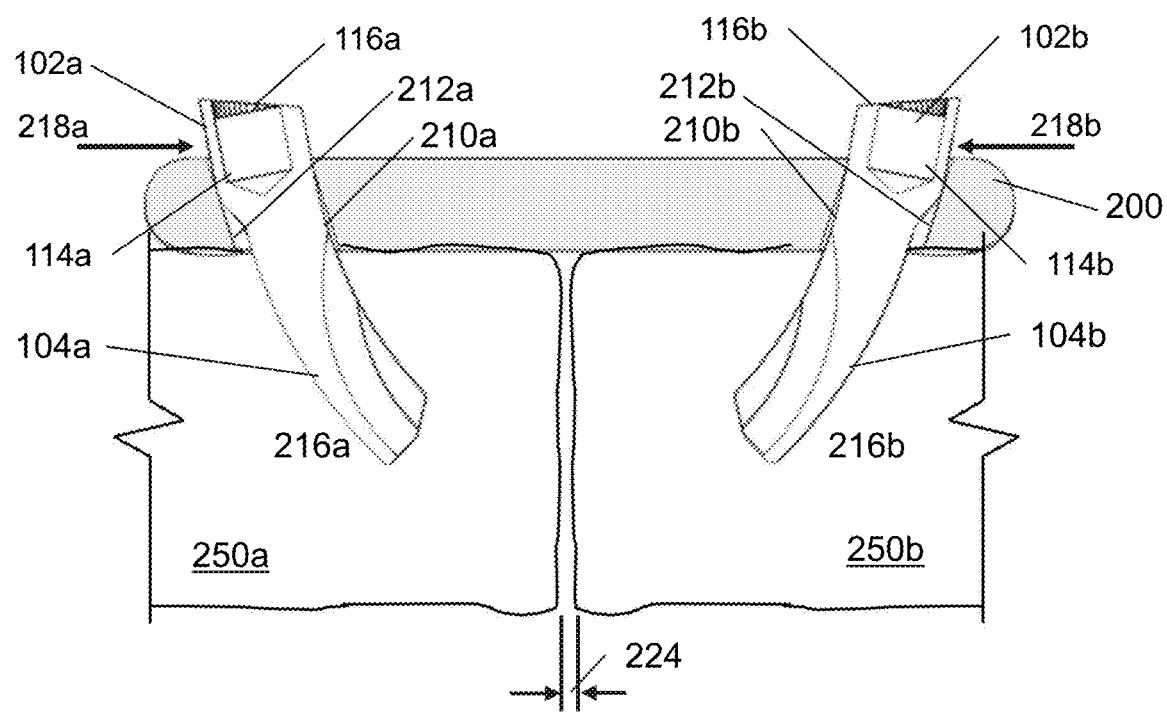

FIG. 3D illustrates the situation where the non-torsional force continues to be applied onto the proximal end 116a of the head portion 102a as the first head portion is pushed farther into the first aperture 210a. The interaction between the inwardly sloped surface 212a of the aperture 210a and the offset portion 114a of the head portion 102a forces the head portion to keep moving in the transverse direction ad indicated by arrow 218a. As discussed above, the transverse movement of the head portion 102a also causes additional transverse movement of the elongated body portion 104a, which causes the boney structure 250a to also move in the direction of arrow 218a towards the boney structure 250b.

Simultaneously, a second non-torsional force continues to be applied onto the proximal end 116b of the head portion 102b as the head portion is pushed farther into the first aperture 210a. The interaction between the inwardly sloped surface 212b of the aperture 210b and the offset portion 114b of the head portion 102b forces the head portion to keep moving in the transverse direction as indicated by arrow 218b. As discussed above, the transverse movement of the head portion 102b also causes additional transverse movement of the elongated body portion 104a, which causes the boney structure 250b to also move in the direction of arrow 218a and towards the boney structure 250a. The relative movement between the boney structure 250a and the boney structure 250b causes the gap 224 to significantly narrow.

Figure 3E:
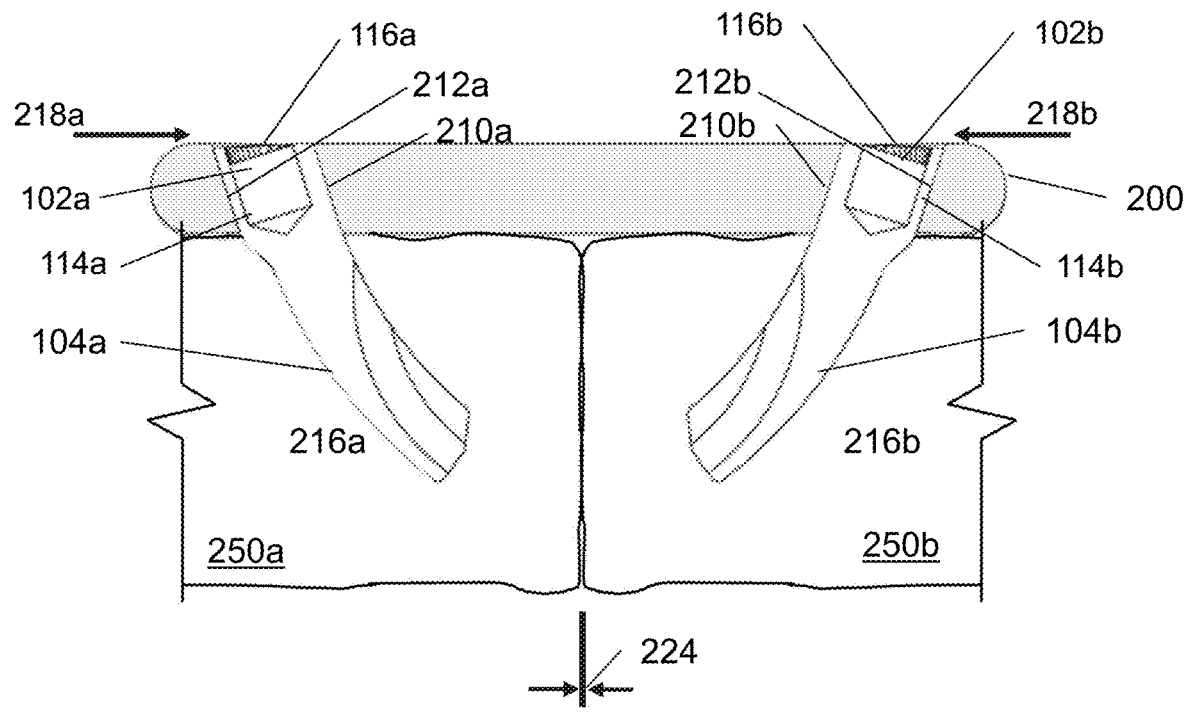

FIG. 3E illustrates the situation where the head portion 102a has been pushed completely into the aperture 210a. As explained above, the interaction between the inwardly sloped surface 212a of the aperture 210a and the offset portion 114a of the head portion 102a has forced the head portion to continue to move transversely in the direction of the arrow 218a. The transverse movement of the head portion 102a also cause transverse movement of the elongated body portion 104a, which caused the boney structure 250a to compress against the boney structure 250b.

Similarly, the head portion 102b has been pushed completely into the aperture 210b. As explained above, the interaction between the inwardly sloped surface 212b of the aperture 210b and the offset portion 114b of the head portion 102b has forced the head portion to move transversely in the direction of the arrow 218b. The transverse movement of the head portion 102b also caused the transverse movement of the elongated body portion 104b, which caused the boney structure 250b to compress against the boney structure 250a. The gap 224 is now closed as the boney structure 250a is pressed against the boney structure 250b. The magnitude or height of the offset of the anchor head portions 102a-102b and the angle of slope of the engagement surfaces 212a and 212b determine the amount of compression achieved.

In certain embodiments, the oversized geometry of the offset portion 114 causes a light press fit between the anchor head portion 114 and an aperture of an implant. Thus, in some embodiments, the offset portion 114 may be an oversized geometric volume which contacts a surface of the aperture of an implant. These are cylindrical surfaces which will largely be concentric in the final position, and in the offset portion 114 they may have an incrementally larger radius than the underside of the surface in the aperture resulting in being wedged together in the final position—which assists in preventing the anchor from "backing out" of the respective aperture. In yet other embodiments, other anti-back methods and techniques may also be employed, such as blocker plates, retaining rings, and locking screws.

Other Embodiments

For purposes of simplification, the implant embodiments discussed above have illustrated and described with an implant and two anchors. However, the present invention contemplates the use of implant embodiment systems using more than two anchors.

In alternative embodiments, one or more anchors may be a traditional anchor without an offset head portion. For instance in FIGS. 3A through 3E, the anchor 100b may be replaced with a traditional anchor (either threaded or nonthreaded) having a symmetrical head portion. Similarly, the aperture 210b may be replaced with a traditional concentric aperture designed to accommodate a traditional anchor with a concentric or symmetrical head. In this alternative embodiment, the symmetrical head and concentric aperture would not cause a transverse shift as explained above. Consequently, significant compression due to movement would not occur on the side of the implant having a traditional anchor. For example in FIG. 3C, if the anchor 100b is replaced with a traditional anchor and the aperture 210b is replaced with a symmetrical aperture, then only the boney structure 250a would move toward the boney structure 250b. The boney structure 250b would remain relatively stationary in this alternative embodiment.

Although the above discussion focuses on compressing boney structures together or compressing a boney structure against an implant, the above anchors and methods could also be used to cause distraction between a first boney structure and a second boney structure via a modification of the anchors and implants. By reversing or flipping the head geometry (i.e. offset portions 114) of the anchors 100a-100b and reversing or flipping the engagement surfaces and geometries of the respective apertures 210a-210b of the implants 200, distraction of boney structures can be achieved by using the methods described above.

While the above example uses anchors 100 with the two aperture implants 200, implants may have two, four, six or more apertures and the corresponding number of anchors and still be within the scope of this invention.

Figure 4:
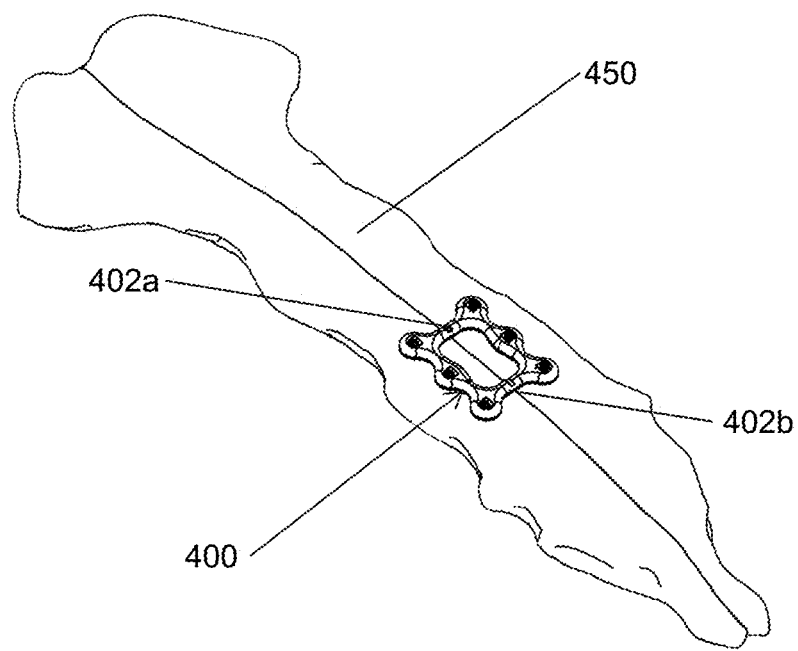
FIG. 4 is an alternative embodiment using six anchors.

For instance, FIG. 4 depicts a perspective view of a six anchor implant 400 joining a divided and re-aligned sternum 450. The implant 400 and the associated six anchors fixes and holds the sternum 450 together following a cardiac procedure.

In yet other embodiments, various components, for example the anchors 100 may be made from nickel titanium (also known as Nitinol®) or another shape memory alloy. The anchor would have a very specific shape at a cooler temperature, such as room temperature. Once inserted into a human body, the metal would rise to a body temperature which will cause the anchor to change shape to enhance compression.

For instance, at or below room temperature a straight anchor might be inserted. At body temperature, the straight anchor turns into a curved anchor and applies additional compression or distraction. Similarly, a curved anchor could turn into a straight anchor at body temperature to enhance either compression or distraction.

In yet other embodiments, the implant or parts of the implant may be formed of a shape memory alloy. For example in FIG. 4, the joining members 402a and 402b may be made of Nitinol® and be straight at a cooler temperature, such as room temperature. Once inserted into a human body and the surgical procedure completed, the temperature of the joining members 402a and 402b would rise to a body temperature which will cause the joining members to curve. As joining members 402a-402b curve (either inwards or outwards), the joining members will begin to pull on the rest of the implant, which will cause additional compression.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

Any advantages and benefits described may not apply to all embodiments of the invention. When the word "means" is recited in a claim element, Applicant intends for the claim element to fall under 35 USC 112(f). Often a label of one or more words precedes the word "means". The word or words preceding the word "means" is a label intended to ease referencing of claims elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word "means" are not intended to fall under 35 USC 112(f).

The foregoing description of the embodiments of the invention has been presented for the purposes of illustration and description. It is not intended to be exhaustive or to limit the invention to the precise form disclosed. Many combinations, modifications and variations are possible in light of the above teaching. For instance, in certain embodiments, each of the above described components and features may be individually or sequentially combined with other components or features and still be within the scope of the present invention. Undescribed embodiments which have interchanged components are still within the scope of the present invention. It is intended that the scope of the invention be limited not by this detailed description, but rather by the claims.

Some embodiments include: a method for joining a first boney structure to a second boney structure, the method comprising: positioning a supra implant adjacent to the first boney structure and to the second boney structure; introducing a first distal end of a first non-threaded anchor into a first non-threaded aperture defined within the supra implant, introducing a second distal end of a second non-threaded anchor into a second non-threaded aperture defined within the supra implant, applying a first non-torsional force onto a first proximal end of a first offset head of the first non-threaded anchor to drive the first distal end through the first aperture, and into the first boney structure along a first trajectory; applying a second non-torsional force onto a second proximal end of a second offset head of the second non-threaded anchor to drive the second distal end through the second aperture, and into the second boney structure along a second trajectory; continuing to apply the first non-torsional force onto the first proximal end of the first offset head as the first offset head reaches a first sloped engagement surface of the first aperture; continuing to apply the second non-torsional force onto the second proximal end of the second offset head as the second offset head reaches a second sloped engagement surface of the second aperture; causing the first offset head to interact with the first engagement surface of first aperture to move the first offset head transversely with respect to the first trajectory to cause the first boney structure to also move transversely with respect to the first trajectory; and causing the second offset head to interact with the second engagement surface of second aperture to move the second offset head transversely with respect to the second trajectory to cause the second boney structure to also move transversely with respect to the first trajectory.

The method above wherein the transverse movement of the first boney structure and a transverse movement of the second boney structure causes compression between the first boney structure and the second boney structure.

The method above wherein a transverse movement of the first boney structure and the transverse movement of the second boney structure causes distraction between the first boney structure and the second boney structure.

The method above and further comprising: introducing a third distal end of a third non-threaded anchor into a third non-threaded aperture defined within the supra implant, applying a third non-torsional force onto a third proximal end of a third offset head of the third non-threaded anchor to drive the third distal end through the third aperture, and into the first boney structure along a third trajectory; continuing to apply the third non-torsional force onto the third proximal end of the third offset head as the third offset head reaches a third sloped engagement surface of the third aperture; and causing the third offset head to interact with the third engagement surface of third aperture to move the third offset head transversely with respect to the third trajectory to cause the first boney structure to also move transversely with respect to the third trajectory.

The method above and further comprising: introducing a fourth distal end of a fourth non-threaded anchor into a fourth non-threaded aperture defined within the supra implant, applying a fourth non-torsional force onto a fourth proximal end of a fourth offset head of the fourth non-threaded anchor to drive the fourth distal end through the fourth aperture, and into the second boney structure along a fourth trajectory; continuing to apply the fourth non-torsional force onto the fourth proximal end of the fourth offset head as the fourth offset head reaches a fourth sloped engagement surface of the fourth aperture; and causing the fourth offset head to interact with the fourth engagement surface of fourth aperture to move the fourth offset head transversely with respect to the fourth trajectory to cause the second boney structure to also move transversely with respect to the fourth trajectory.

The method above wherein the causing the first offset head to interact with the first engagement surface of first aperture to move the first offset head transversely comprises applying a first force from the first engagement surface onto a first offset portion of the first offset head.

The method above wherein the causing the second offset head to interact with the second engagement surface of second aperture to move the second offset head transversely comprises applying a second force from the second engagement surface onto a second offset portion of the second offset head.

The method above wherein a direction of movement of the first offset head is opposite to a direction of the movement of the second offset head.

The method above wherein a direction of movement of the first offset head is linearly aligned with the direction of the movement of the second offset head.

Additionally, there also may be a supra implant system for joining boney structures comprising: a first non-threaded anchor having a first center axis including a first non-threaded elongated body; a first non-threaded head coupled to a proximal end of the elongated body, the first head including, a concentric portion of the first head that is substantially concentric to the center axis, and an offset portion of the first head that is offset from the center axis; a second non-threaded anchor having a second center axis including, a second non-threaded elongated body; a second non-threaded head coupled to a proximal end of the elongated body, the second head including, a concentric portion of the second head that is substantially concentric to the center axis, and an offset portion of the second head that is offset from the center axis; a supra implant including, a first end portion including a first aperture defined therein, the first aperture having a first sloped engagement surface, the first aperture sized and shaped to fully accept the first head only when the first sloped engagement surface engages the offset portion of the first head to force a first transverse movement of the first head; a second end portion including a second aperture defined therein, the second aperture having a second sloped engagement surface, the second aperture sized and shaped to fully accept the second head only when the second sloped engagement surface engages the offset portion of the second head to force a second transverse movement of the second; and a main body portion joining the first end portion to the second end portion.

The above system wherein the first sloped engagement surface is a first force applying surface sized and shaped to assert a first transverse force on the offset portion of the first head as the offset portion of the first head slidingly engages the first force applying surface.

The above system wherein the first aperture incudes a first opposing sloped surface opposing the first sloped engagement surface and the second aperture includes a second opposing sloped surface opposing the second sloped engagement surface.

The above system wherein the first aperture is longitudinally aligned with the second aperture.

The above system, further comprising: a third non-threaded anchor having a third center axis including, a third non-threaded elongated body; a third non-threaded head coupled to a proximal end of the elongated body, the third head including, a concentric portion of the third head that is substantially concentric to the center axis, an offset portion of the third head that is offset from the center axis; and a third aperture defined therein, the third aperture having a third sloped engagement surface, the third aperture shaped to fully accept the third head only when the third sloped engagement surface engages the offset portion of the third head to force a third transverse movement of the third head.

The above system, further comprising: a fourth non-threaded anchor having a fourth center axis including, a fourth non-threaded elongated body; a fourth non-threaded head coupled to a proximal end of the elongated body, the fourth head including, a concentric portion of the fourth head that is substantially concentric to the center axis, an offset portion of the fourth head that is offset from the center axis; and a fourth aperture defined therein, the fourth aperture having a fourth sloped engagement surface, the fourth aperture shaped to fully accept the fourth head only when the fourth sloped engagement surface engages the offset portion of the fourth head to force a fourth transverse movement of the fourth head.

The invention claimed is:

1. A method for joining a first boney structure to a second boney structure, the method comprising:
    positioning a supra implant adjacent to the first boney structure and to the second boney structure;
    introducing a first distal end of a first non-threaded anchor into a first non-threaded aperture defined within the supra implant,
    introducing a second distal end of a second non-threaded anchor into a second non-threaded aperture defined within the supra implant,
    applying a first non-torsional force onto a first proximal end of a first offset head of the first non-threaded anchor to drive the first distal end through the first aperture and to pierce the first boney structure as the first distal end is driven along a first trajectory;
    applying a second non-torsional force onto a second proximal end of a second offset head of the second non-threaded anchor to drive the second distal end through the second aperture and to pierce the second boney structure as the second distal end is driven along a second trajectory;
    continuing to apply the first non-torsional force onto the first proximal end of the first offset head as the first offset head reaches a first sloped engagement surface of the first aperture to continue to penetrate;
    continuing to apply the second non-torsional force onto the second proximal end of the second offset head as the second offset head reaches a second sloped engagement surface of the second aperture;
    continuing to apply the first non-torsional force onto the first proximal end of the first offset head to cause the first offset head to interact with the first engagement surface of first aperture to move the first offset head transversely with respect to the first trajectory to cause the first boney structure to also move transversely with respect to the first trajectory; and
    continuing to apply the second non-torsional force onto the second proximal end of the second offset head to cause the second offset head to interact with the second engagement surface of second aperture to move the second offset head transversely with respect to the second trajectory to cause the second boney structure to also move transversely with respect to the first trajectory.

2. The method of claim 1, wherein the transverse movement of the first boney structure and the transverse movement of the second boney structure causes compression between the first boney structure and the second boney structure.

3. The method of claim 1, further comprising:
    introducing a third distal end of a third non-threaded anchor into a third non-threaded aperture defined within the supra implant,
    applying a third non-torsional force onto a third proximal end of a third offset head of the third non-threaded anchor to drive the third distal end through the third aperture and into the first boney structure along a third trajectory;
    continuing to apply the third non-torsional force onto the third proximal end of the third offset head as the third offset head reaches a third sloped engagement surface of the third aperture; and
    continuing to apply the third non-torsional force onto the third proximal end of the third offset head to cause the third offset head to interact with the third engagement surface of third aperture to move the third offset head transversely with respect to the third trajectory to cause the first boney structure to also move transversely with respect to the third trajectory.

4. The method of claim 3, further comprising:
    introducing a fourth distal end of a fourth non-threaded anchor into a fourth non-threaded aperture defined within the supra implant,
    applying a fourth non-torsional force onto a fourth proximal end of a fourth offset head of the fourth non-threaded anchor to drive the fourth distal end through the fourth aperture and into the second boney structure along a fourth trajectory;
    continuing to apply the fourth non-torsional force onto the fourth proximal end of the fourth offset head as the fourth offset head reaches a fourth sloped engagement surface of the fourth aperture; and
    continuing to apply the fourth non-torsional force onto the fourth proximal end of the fourth offset head to cause the fourth offset head to interact with the fourth engagement surface of fourth aperture to move the fourth offset head transversely with respect to the fourth trajectory to cause the second boney structure to also move transversely with respect to the fourth trajectory.

5. The method of claim 1, wherein the causing the first offset head to interact with the first engagement surface of first aperture to move the first offset head transversely comprises applying a first force from the first engagement surface onto a first offset portion of the first offset head.

6. The method of claim 1, wherein the causing the second offset head to interact with the second engagement surface of second aperture to move the second offset head transversely comprises applying a second force from the second engagement surface onto a second offset portion of the second offset head.

7. The method of claim 1, wherein a direction of movement of the first offset head is opposite to a direction of the movement of the second offset head.

8. The method of claim 1, wherein a direction of movement of the first offset head is linearly aligned with the direction of the movement of the second offset head.

\* \* \* \* \*